United States Patent [19]
Leibinger et al.

[11] Patent Number: 4,763,548
[45] Date of Patent: Aug. 16, 1988

[54] SCREWDRIVER, PARTICULARLY FOR SURGICAL PURPOSES

[75] Inventors: Karl Leibinger, Tuttlingen-Mohringen; Franz Leibinger, Mühlheim-Stetten, both of Fed. Rep. of Germany

[73] Assignee: Oswald Leibinger GmbH, Mühleim-Stetten, Fed. Rep. of Germany

[21] Appl. No.: 919,245

[22] Filed: Oct. 15, 1986

[30] Foreign Application Priority Data

Nov. 6, 1985 [DE] Fed. Rep. of Germany ....... 3539502

[51] Int. Cl.⁴ ............................................. B25B 23/10
[52] U.S. Cl. ......................................... 81/453; 81/438
[58] Field of Search .......... 81/436, 438, 439, 451–453, 81/177.1; 279/30

[56] References Cited

U.S. PATENT DOCUMENTS

| | | | |
|---|---|---|---|
| 1,049,650 | 1/1913 | Benjamin | 81/177.1 X |
| 2,010,210 | 8/1935 | Witt | 279/30 X |
| 2,302,691 | 11/1942 | Green | 81/453 |
| 2,370,407 | 2/1945 | McCartney | 81/453 |
| 2,762,408 | 9/1956 | Baldwin | 81/453 |
| 2,775,276 | 12/1956 | Rossner | 81/177.1 |
| 2,933,114 | 4/1960 | Bystrom | 81/453 |
| 2,952,285 | 9/1960 | Röösli | 81/453 |
| 3,436,086 | 4/1969 | Glenzer | 279/30 |
| 3,498,351 | 3/1970 | Edwards et al. | 81/453 |
| 3,529,842 | 9/1970 | Benjamin et al. | 279/30 |
| 3,957,096 | 5/1976 | Rodman | 81/177.1 |
| 4,093,008 | 6/1978 | Martin | 81/177.1 |

FOREIGN PATENT DOCUMENTS 3003118 8/1980 Fed. Rep. of Germany.

OTHER PUBLICATIONS

Drawing No. 10958/9014 of the Firm of Robert Schroder, 5600 Wuppertal, Mar. 1969.

*Primary Examiner*—Frederick R. Schmidt
*Assistant Examiner*—Bradley I. Vaught
*Attorney, Agent, or Firm*—Mason, Fenwick & Lawrence

[57] ABSTRACT

A screwdriver is provided which engages the head of the screw, and also grips the screw. The screwdriving and gripping assemblage may be readily interchanged with another in the handle of the screwdriver. Opening and closing of gripping jaws is effective by the sliding of an outer sleeve which surrounds another sleeve of which the gripping jaws form a part, and which other sleeve is slidable on the shaft of the screwdriver. The handle comprises a front part and a rear part which are rotatably connected together for rotation of the forward part and of the screwdriver shaft, while the rear part is held fixed.

10 Claims, 3 Drawing Sheets

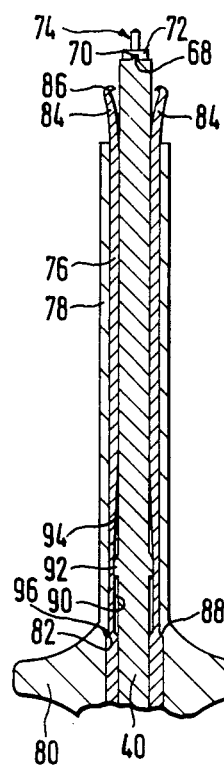
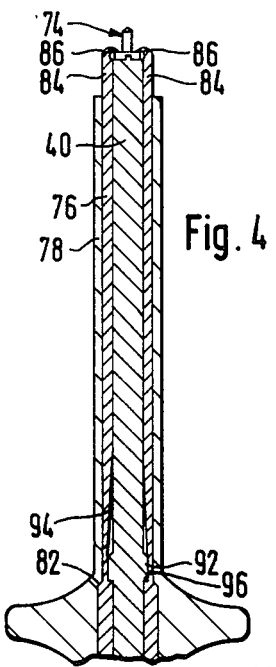
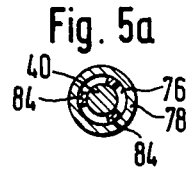
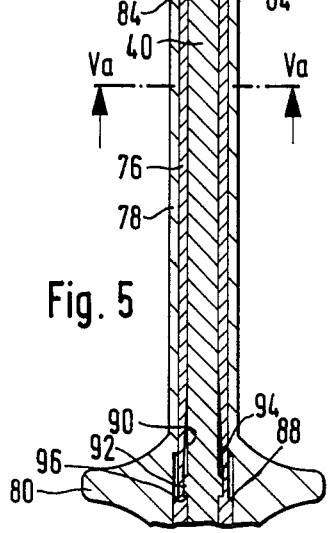
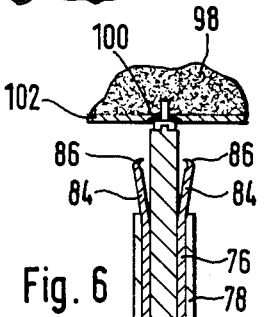
Fig. 3
Fig. 4
Fig. 5a
Fig. 5
Fig. 6

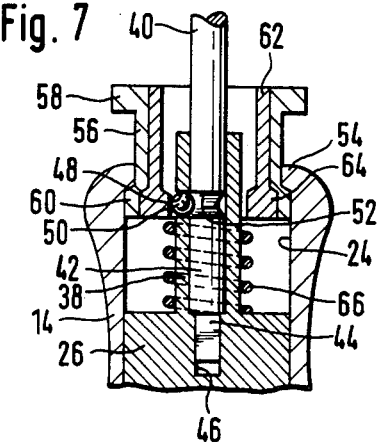
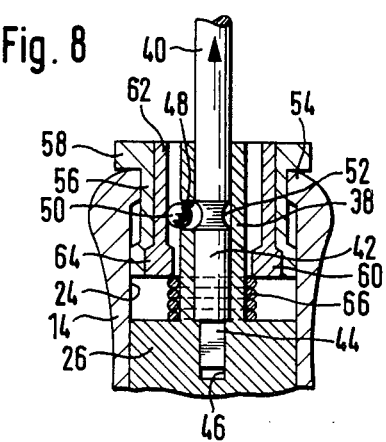

4,763,548

SCREWDRIVER, PARTICULARLY FOR SURGICAL PURPOSES

BACKGROUND OF THE INVENTION

This invention relates to a screwdriver capable of gripping and driving a screw.

A screwdriver of this type is known from U.S. Pat. No. 3,498,351, which can be used advantageously for surgical and other difficult screwing processes. However, with this screwdriver, it is not possible to turn screws with different heads, for example, a longitudinal slot, a recessed slot, a Phillips head, an Imbus-head and a similar head, but a different screwdriver must be used for each type of screw. Especially for surgical processes, a large number of other instruments are required so that many different instruments must be available for an operation. In addition, sterilization of the known screwdriver is not very simple because of the numerous parts that are fitted into one another and which can be slid with respect to one another. Also, a perfect and sensitive operatability of this screwdriver under difficult conditions, for example, while using a surgical glove, is not ensured.

There is disclosed in Drawing No. 10958/9014 of the firm of Robert Schroder, 5600 Wuppertal, of March 1969, a screwdriver having interchangeable screwing tools. In this screwdriver, a spring-loaded sliding sleeve having a lockball mechanism is used for the locking of the tool shaft. However, neither a screw removal device having a gripping element of the screwhead is provided, nor a two-part handle that can be operated conveniently and securely.

The dividing of a screwdriver handle is shown in DE-OS No. 30 03 118. There is disclosed a bent screwdriver that is anchored firmly in a center part of the handle and has two balls that are pivotable at both ends of the handle, which make possible a circular motion of the rear end of the blade around the blade axis. This known dividing of the handle cannot be used in a screwdriver as herein disclosed.

SUMMARY OF THE INVENTION

A screwdriver is provided which is capable of both driving a screw and gripping a screw, and which provides for the ready interchangeability of the shaft, and the associated parts, so that a plurality of shafts with different screw engagement configurations may be used. Connected to a handle is an assemblage including a shaft having a tool at one end for engaging a screw, outwardly of which is a screw gripping apparatus which includes a clamping jaw sleeve of resilient material having at the outer end thereof a pair of opposed clamping jaws, which are normally elastically urged outwardly. An outer clamping sleeve is slidable on the inner clamping jaw sleeve, in a forward position urging the clamping jaws towards each other, and in a rearward position releasing the clamping jaws for outward or spreading movement. Stops are provided for limiting the longitudinal movement of the clamping jaw sleeve with respect to the shaft in both directions, and stops are also provided for limiting longitudinal movement of the clamping sleeve with respect to the clamping jaw sleeve in the inward direction, away from the tool. The handle is in two parts, a front part being connected for rotary movement relative to the rear part. The shaft is disconnectable from the handle by a mechanism including a hollow post in the front part of the handle which receives the rear end of the tool shaft. A peripheral groove is in the rear end of the tool shaft, and a hollow post has a lateral opening opposite said peripheral groove when the shaft is seated in it; a ball is moveable radially in the lateral opening and into the groove. A sliding sleeve is provided in the front part of the handle which, in one position, urges the ball into the groove, to thereby latch the shaft to the handle, and a spring urges this sleeve into the noted position. The sleeve may be manually moved against the spring, so as to permit the ball to move out of the groove, thereby unlatching the shaft and permitting its removal from the handle.

Among the objects of the present invention is to provide a screwdriver having a screw gripping apparatus, and which will avoid a large turning force on the screw. Another object is to provide a screwdriver which is constructed so that only the strength of the fingers provide the torque for the driving shaft. Still another object of the present invention is the provision of a screwdriver construction in which screwdriving tools of different configurations may be readily interchanged into a handle. Other objects and many of the attendant advantages of the present invention will be readily understood from a consideration of the following specification, claims and the appended drawings.

BRIEF DESCRIPTION OF THE DRAWINGS

FIGS. 3 to 5 and 6 are axial sections of the forward part of the screwdriver in four successive stages of the removal and insertion of a bone screw;

FIG. 5a is a section along the Line Va—Va in FIG. 5; and

FIGS. 7 and 8 are enlarged cross-sectional views of the front end of the handle in two different operating positions.

DESCRIPTION OF THE PREFERRED EMBODIMENT

Figure 1:
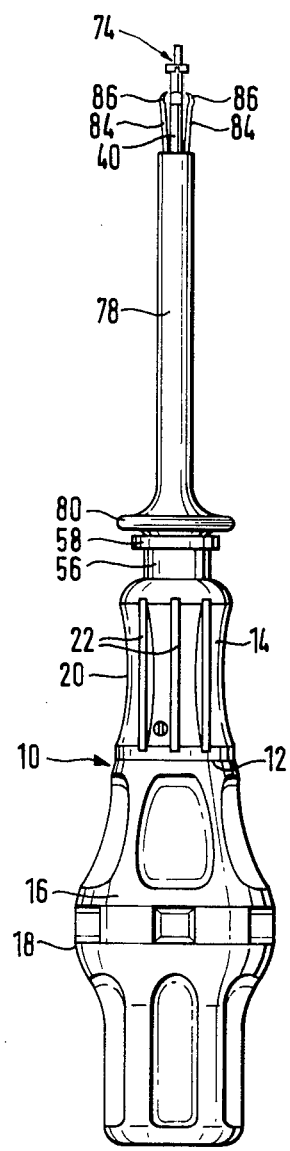
FIG. 1 is an elevational view of a screwdriver in accordance with the present invention with a clamping sleeve pulled back.
Figure 2:
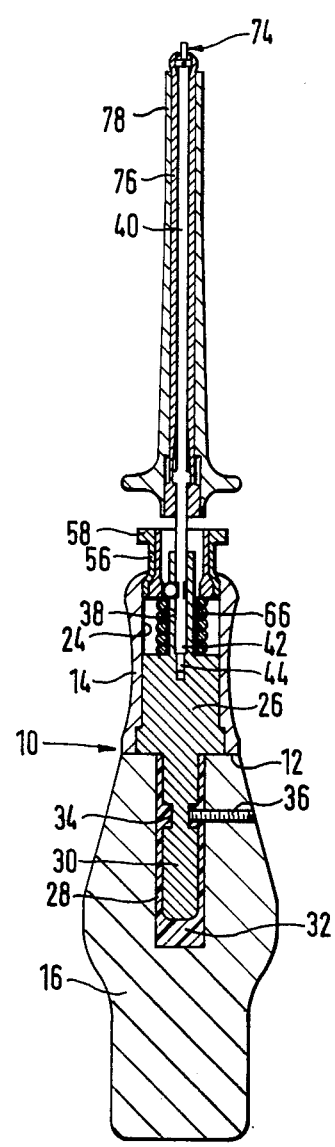
FIG. 2 is an axial section of the screwdriver of FIG. 1, with the clamping sleeve pushed forward.

The screwdriver 10 shown in the figures has a handle divided into two axially adjacent parts along a radial plane 12, namely into a front part 14 and a rear part 16. The rear part 16 has a bulged-out surface 18 that is ergonomically favorably shaped to the inside surface of the hand, while the front part 14 has a slightly concave surface 20 having longitudinal ribs 22 for turning it by means of the finger tips of the thumb and the index finger and possibly the middle finger. The front part 14 has a recess 24 that is open toward the front into which an insertion piece 26 is firmly inserted. On the insertion piece 26, an arbor or male part 30 is located that projects backwards into a recess 28 of the rear part 16, a bearing 32 of slidable material being inserted between the arbor 30 and the recess 28. The arbor 30 has an annular groove 34 into which a stud screw 36 is inserted with play, stud screw 36 extending through a bore in the rear part 16 of the grip. As a result, the front part 14 may be rotated with respect to the rear part 16.

From the center of the insertion piece 26, a hollow-cylinder-shaped post 38 projects toward the front that projects beyond the open front end of the front part 14. Into the post 38, the rear end 42 of a shaft 40 is inserted; a polygon stud 44 located on the rear end 42 is inserted into a corresponding shaped polygonal socket 46 of the insertion piece 26. As a result, the shaft 40 is forced to rotate with the front part 14 of the grip.

As shown in FIG. 7, the post 38 has a radial opening 48 in which a radially movable ball 50 is disposed. When the rear end 42 of the shaft 40 is completely inserted into the post 38, a circumferential groove 52 of the shaft 40 is located at the same level as the opening 48 with the ball 50. The ball 50 can therefore penetrate into the groove 52. At its front end, the front part 14 has a ring-shaped taper 54 that rests against the exterior side of an essentially cylindrical sliding sleeve 56. The sliding sleeve 56 has a radially projecting front stop ring 58 and a corresponding rear stop ring 60 so that, with respect to the front part 14, it is axially slidable between the positions of FIG. 7 and FIG. 8. The sliding sleeve 56 has a metallic insert 62 that forms its interior wall, said insert 62 also being shaped essentially cylindrically and at its rear end, having a ring-shaped thickening 64.

A compression spring 66 is, on the one side, supported at the front side of the insertion piece 26 and, on the other side, at the thickening 64 and urges the sliding sleeve 56 into the position of FIG. 7. In this position, the thickening 64 rests against the ball 50 and presses it into the groove 52. As a result, the shaft 40 is locked to the post 38. When the sliding sleeve 56 is pulled back from the position of FIG. 7 into the position of FIG. 8 against the force of the spring 66, for which the front stop ring 58 can be used, the thickening 64 disengages from the ball 50 so that it can come out of the groove 52 and the shaft 40 can be pulled out of the post 38. Subsequently, a shaft of another tool can be inserted, after which the sliding sleeve 56 is let go and by means of the force of the spring 66 snaps back into the position shown in FIG. 7. As a result, the shaft of the new tool is securely locked.

Details of the screw removal device and of the tool shaft interacting with it are shown best in FIGS. 3 to 6. In the case of the herein disclosed embodiment, the tool located at the front end of the shaft 40 is a screwdriver blade 68 for engagement with the straight longitudinal slot 70 in the head 72 of a bone screw 74. In the position of FIG. 3, the clamping jaw sleeve 76 that surrounds the shaft 40 and is disposed so that it can slide on it, and the clamping sleeve 78 that surrounds the clamping jaw sleeve 76 and can also be slid longitudinally with respect to it, are in a pulled-back position. The pulling-back of the clamping jaw sleeve 76 and of the clamping sleeve 78 takes place by means of an actuating ring 80 forming one piece with the clamping sleeve 78. This actuating ring 80 can be gripped by the fingers of the hand guiding the instrument. The clamping sleeve 78 extends essentially cylindrically and has a rearwardly facing shoulder 82 close to the actuating ring 80. The clamping jaw sleeve 76 is essentially cylindrical at its rear end and at its front end comprises two diametrically opposite clamping jaws 84 that extend from the rear end and in the position of FIG. 3 are unstressed by the clamping sleeve 78; these jaws 84 spring slightly outward because of inherent elasticity of the material. At the front end, the clamping jaws 84 have grippers 86 that are bent inwardly.

The clamping jaw sleeve 76, at its section extending close to the actuating ring 80, on its exterior side, has a shoulder 88 that interacts with the shoulder 82 of the clamping sleeve 78 that limits the pulling-back of the clamping sleeve 78 with respect to the clamping jaw sleeve 76 to the position shown in FIG. 4. Next to this step 88, on the interior side of the clamping jaw sleeve 76, a recess 90 is provided that extends around the interior circumference of the clamping jaw sleeve 76; a ring-shaped projection 92 on the exterior of the shaft 40 can be longitudinally slid in recess 90 between the end stops 94 and 96. The two stops 94 and 96 limit the relative movement between the shaft 40 and the clamping jaw sleeve 76 in both directions.

For the removal of a bone screw 74 from a selection of screws (not shown), the blade 68 is first inserted into the longitudinal slot 70 of the bone screw 74, while the clamping jaw sleeve 76 and the clamping sleeve 78 are located in the pulled-back position shown in FIG. 3. Then, by means of the actuating ring 80, the clamping sleeve 78 is pushed forward into the position of FIG. 4. Because of the slightly spread-out clamping jaws 84, clamping sleeve 78 pushes the clamping jaw sleeve 76 forwardly until the rear stop 96 of the recess 90 rests against the projection 92 of the shaft 40. With the further advancing of the clamping sleeve 78, the clamping jaws 84 are pressed inwardly, and the grippers 86 converge behind the head 72 of the bone screw 74, as shown in FIG. 4. After the complete advancing of the clamping sleeve 78 into the position of FIG. 5, by means of which the shoulders 82 and 88 move away from one another, the bone screw 74 is now, by means of the interaction of the blade 68 and the grippers 86, completely fixed in the screwdriver. In this condition, the bone screw 74 can be screwed into a bone 98, possibly through an opening 100 of a bone plate 102 to be fixed to the bone 98, until the grippers 86 come to rest lightly against the exterior face of the bone plate 102. Advantageously, shortly before this position, the actuating ring 80 and thus the clamping sleeve 78 is pulled back to the position of FIG. 3, causing the clamping jaws 84 to be released and spring outwardly. As soon as the shoulders 82 and 88 come to rest against one another, the clamping jaw sleeve 76 is also pulled back until the front stop 94 of the recess 90 against abuts the projection 92, as shown in FIG. 6. This whole release process of the bone screw 74 can take place very rapidly, (thus practically) during the screwing-in process, by the pulling-back of the actuating ring 80 and subsequently, the bone screw 74 can be tightened completely, as shown in FIG. 6.

While the more extensively stressed parts of the screwdriver, such as the shaft 40, the blade 68, the clamping jaw sleeve 76, the clamping sleeve 78, the insert 62, the ball 50 and the insertion piece 26 with the post 38, as mentioned above, are made preferably of rustproof steel or highly compressed titanium, the outer parts of the handle and of the sliding sleeve 56 consist preferably of fully sterilizable plastic, such as tetrafluoroethylene.

We claim:
1. A screwdriver comprising:
(A) a handle,
(B) a shaft extending from said handle and having a free end with a screw-engaging blade,
(C) means for connecting said shaft to said handle, and
(D) screw clamping means comprising:
(i) clamping jaws of elastic material urged to open position away from said shaft by the elasticity thereof, and
(ii) operating means for said clamping jaws comprising:
(a) a longitudinally movable actuator movable only outward and away from said handle,

(b) means for causing said jaws to be first opened and then retracted towards said handle upon longitudinal retraction movement of said actuator toward said handle, and (c) means for causing said clamping jaws to advance away from said handle and then to be closed upon longitudinal advancing movement of said actuator away from said handle comprising a projection on said shaft, a sleeve connected to said clamping jaws and having a pair of axially spaced stops engageable by said projection in different axial positions thereof, an external shoulder on said clamping jaw sleeve, and a clamping sleeve connected to said actuator for engaging said clamping jaws and having a stop shoulder thereon engageable with said external shoulder of said clamping jaw sleeve;

whereby, said clamping jaws may be sequentially opened, retracted, advanced and closed by only longitudinal movement of said actuator.

2. The screwdriver of claim 1, said elastic clamping jaws being the only elastically deformable element of said screw clamping means.

3. The screwdriver of claim 1, said handle comprising a front part and a rear part, and means connecting said parts for relative axial rotation.

4. The screwdriver of claim 3, wherein said connecting means for said handle parts comprises a male element extending from one of said handle parts, and a female element in the other of said handle parts, said male element being positioned in said female element.

5. The screwdriver of claim 4, said female element having bearing material therein, said male element engaging said bearing material.

6. The screwdriver of claim 4, said male element having a peripheral groove therein, a screw extending laterally through the other handle part and entering into said groove, said screw having clearance relative to said groove, to thereby permit rotational movement of said male part relative to said female part.

7. The screwdriver of claim 3, the handle rear part having an outwardly bulged surface for engagement by the inside surface of the hand of the user, and wherein said handle front part has a concave surface for engagement by the finger tips of the hand of the user.

8. The screwdriver of claim 7, wherein said handle front part has longitudinal ribs thereon.

9. The screwdriver of claim 1, said means for connecting said shaft to said handle comprising means for releasably connecting said shaft to said handle.

10. The screwdriver of claim 9, said releasable connecting means comprising a peripheral groove in said shaft near the end thereof opposite the blade, said handle comprising a hollow post, said hollow post receiving said opposite end of said shaft, a lateral opening in said hollow post, a ball in said opening and movable into said groove, means for urging said ball into said groove or for permitting said ball to move outwardly of said groove comprising a sleeve slidable on said hollow post having an inwardly directed stop ring for engaging said ball when in juxtaposition therewith, and spring means for urging said sleeve into a position in which said stop ring is in juxtaposition with said ball.

* * * * *